United States Patent
Junger et al.

(10) Patent No.: US 7,455,806 B2
(45) Date of Patent: Nov. 25, 2008

(54) INJECTION MOULDING OF FUNCTIONAL CAVITIES

(75) Inventors: Michael Carl Junger, Queensland (AU); David Sean O'Brien, Queensland (AU); Allan Joseph Hilling Smith, Queensland (AU)

(73) Assignees: William A. Cook Australia Pty. Ltd., Queensland (AU); Cook Incorporated, Bloomington, IN (US)

( * ) Notice: Subject to any disclaimer, the term of this patent is extended or adjusted under 35 U.S.C. 154(b) by 833 days.

(21) Appl. No.: 11/007,849

(22) Filed: Dec. 9, 2004

(65) Prior Publication Data
US 2005/0140068 A1    Jun. 30, 2005

Related U.S. Application Data

(60) Provisional application No. 60/528,421, filed on Dec. 10, 2003.

(51) Int. Cl.
*B29D 22/00* (2006.01)

(52) U.S. Cl. .......... 264/516; 264/572; 264/573
(58) Field of Classification Search .......... 264/516, 264/572–3
See application file for complete search history.

(56) References Cited

U.S. PATENT DOCUMENTS

| | | | | |
|---|---|---|---|---|
| 5,788,917 | A * | 8/1998 | Herlache | 264/572 |
| 6,630,086 | B1 * | 10/2003 | Goral et al. | 264/40.4 |
| 7,029,468 | B2 * | 4/2006 | Honebrink | 604/528 |

* cited by examiner

*Primary Examiner*—Suzanne E. McDowell
(74) *Attorney, Agent, or Firm*—James B. Hunt

(57) ABSTRACT

A mould assembly (60) and a method of use in injection moulding of a part having a functional cavity therein. The mould assembly has a recess (72) to receive a hollow tubular insert (48) intended to be placed in the mould assembly before the injection of a mouldable material into the cavity and to remain in the part after moulding. A gas supply arrangement supplies pressurised gas to the hollow tubular insert at a selected stage during the injection process whereby to form the functional cavity in the part.

8 Claims, 6 Drawing Sheets

INJECTION MOULDING OF FUNCTIONAL CAVITIES

CROSS-REFERENCE TO RELATED APPLICATIONS

This application claims priority of provisional application Ser. No. 60/528,421, filed Dec. 10, 2003.

TECHNICAL FIELD

This invention relates generally to gas assisted injection moulding and more particularly to gas assisted injection moulding to produce moulded parts with functional cavities.

BACKGROUND OF THE INVENTION

Gas assisted injection moulding is a thermoplastic moulding process in which an inert gas is injected into a mouldable material after the moulded material enters a mould. The gas does not mix with the mouldable material but is intended to remain in the middle of the thicker sections of the moulding. By controlling the gas pressure, the quantity of mouldable material injected into mould and the rate of gas flow, a hollow portion can be formed within the moulded part. The gas pressure compensates for the tendency of the mouldable material to shrink at the thicker parts of the moulding, preventing warping and reducing stress. Gas pressure can be relieved before opening the mould.

It has been proposed in the past that the introduction of pressurised gas into the mould may be through the same nozzle that introduces the mouldable material in the part. In the production of some parts it is desirable to induce the pressurised gas at a different location as that of which the mouldable material is introduced. In the past, a gas pin has been used for this purpose, however, this is not applicable where it is desired to produce a functional cavity.

By the term "functional cavity" in this specification it is generally intended to mean a cavity which is formed in an injection moulded part which in the finished product is used for a defined or useful purpose. The defined or useful purpose may be for instance to enable the joining of two ducts or tubes retained in the mould and extending into the mould cavity and moulded into a part to provide a fluid connection between them within the functional cavity. The functional cavity, for instance, may be used to mix two fluid flows or to enable fluid flow from one duct to another within the moulded part.

SUMMARY OF THE INVENTION

In one form therefore, the invention is said to reside in a mould assembly for use in injection moulding of a part having a functional cavity therein, the mould assembly comprising at least a first mould portion and a second mould portion which when joined together define a cavity for moulding the part, at least one of the first and second mould portions having an opening therein for allowing injection of a mouldable material into the cavity, a recess in at least one of the first and second portions, the recess being to receive a hollow tubular insert intended to be placed in the mould assembly before the injection of a mouldable material into the cavity and to remain in the part after moulding and a fluid supply arrangement to supply pressurised fluid to the hollow tubular insert during the injection process whereby to form the functional cavity in the part.

Preferably the pressurised fluid is a gas.

It will be seen therefore that a cavity is formed in the part by injection of gas through the hollow insert during moulding and hence after the moulded part has been completed, access to the cavity formed in the mould can be possible through the hollow insert. Where a moulded part has more than one insert then the functional cavity can act as a flow joiner between a first and second hollow insert.

In a preferred embodiment the mouldable material can be a resilient material and hence a pump and or suction device can be formed. Manipulation of the finished part will enable fluids to be drawn into and expelled from the functional cavity through the hollow tubular insert. For other applications the mouldable material may be any appropriate moulding material.

In the process of injecting mouldable material into the cavity, in one preferred arrangement, a less than complete volume of mouldable material to fill the cavity may be injected and during the injection process, gas at a selected pressure may be injected through the hollow tubular insert substantially into the centre of the desired cavity.

The volume of injected material, the time of injection and the pressure of injection as well as the volume, pressure, temperature and timing of gas injection may be selected to give desirable properties and dimensions to the finished product and the functional cavity.

Alternatively, there may be provided, associated with the mould assembly, a further cavity apart from the mouldable material cavity with a duct extending from the main cavity to the further cavity so that a full shot of mouldable material may be placed into the mould and then when gas is injected into the mould through the hollow tubular insert, excess mouldable material may be passed through the duct from the main cavity into the further cavity. At the end of the moulding cycle the excess mouldable material that has passed into the further cavity can be separated from the moulded part and recycled.

In a still further arrangement the main cavity may be filled by a full shot of mouldable material and upon injection of the pressurised gas, excess material may pass back through the opening, which is in either the first or second mould portion, back into the injection machine. For this purpose injection pressure may be removed or an injection screw rotated in reverse to allow for retraction of some of the moulded material.

The pressurized gas may be air or dry nitrogen or the like.

In a further form the invention may be said to reside in a process of moulding a part with a functional cavity including the steps of providing a mould assembly of the type discussed above, mounting a hollow tubular insert into the recess in the mould assembly, injecting a mouldable material through the opening into the cavity, injecting a gas under pressure through the hollow tubular insert into the cavity and allowing the mouldable material to cool before opening the mould portions to release the moulded part with the hollow tubular insert retained in the moulded part and opening into the functional cavity.

The moulding process may further include the step of cooling the mould before injection of the air to form a skin on the outer surface of the moulded part. When the air is then injected the skin may prevent the cavity extending to the skin of the moulded part.

Where the part to be moulded is to be formed from a resilient material, it may be desirable to carry out an initial moulding step where a hard mouldable material such as a polycarbonate may be injected into a mould in which the insert is received to form ribs around the tubular insert and then the tubular insert with the moulded portion and ribs can be placed into another mould in which the moulding of the part with the hollow tubular insert in a soft material is achieved. The ribs on the tubular insert aid adhesion of the soft outer layer. Hence the functional cavity or void formed in the moulded part could act as a pump when the moulded part is compressed and released.

BRIEF DESCRIPTION OF THE DRAWING

This then generally describes the invention but to assist with understanding, reference will now be made to the accompanying drawings which show preferred embodiments of the invention.

In the drawings.

DETAILED DESCRIPTION

Figure 1:
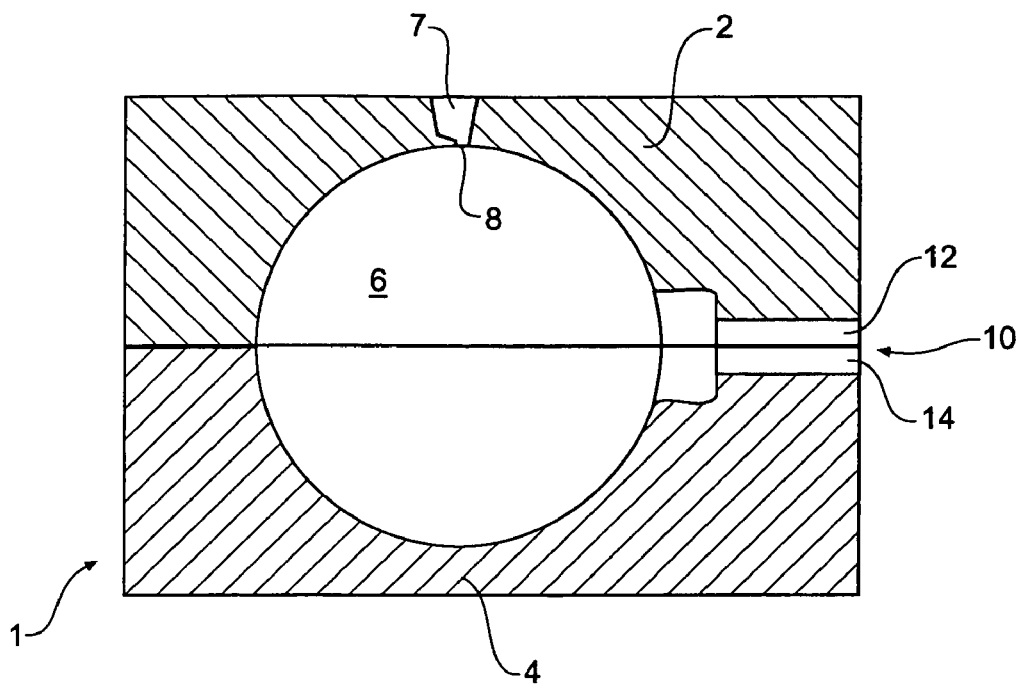
FIG. 1 shows a mould assembly according to a first embodiment of the invention.
Figure 2:
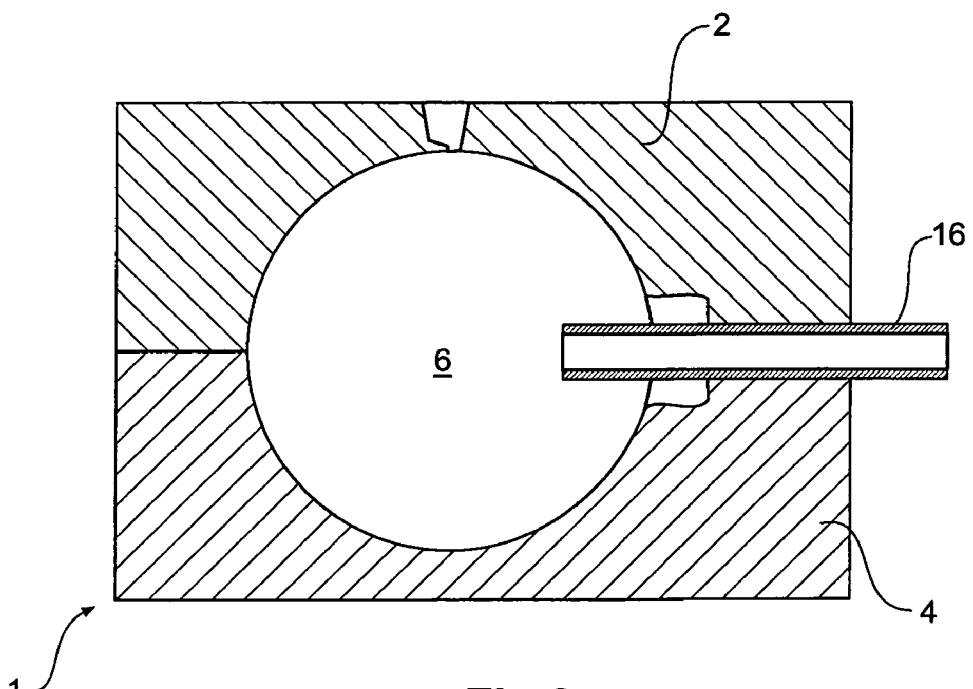
FIG. 2 shows the embodiment of FIG. 1 with a hollow tubular insert received in the mould.
Figure 3:
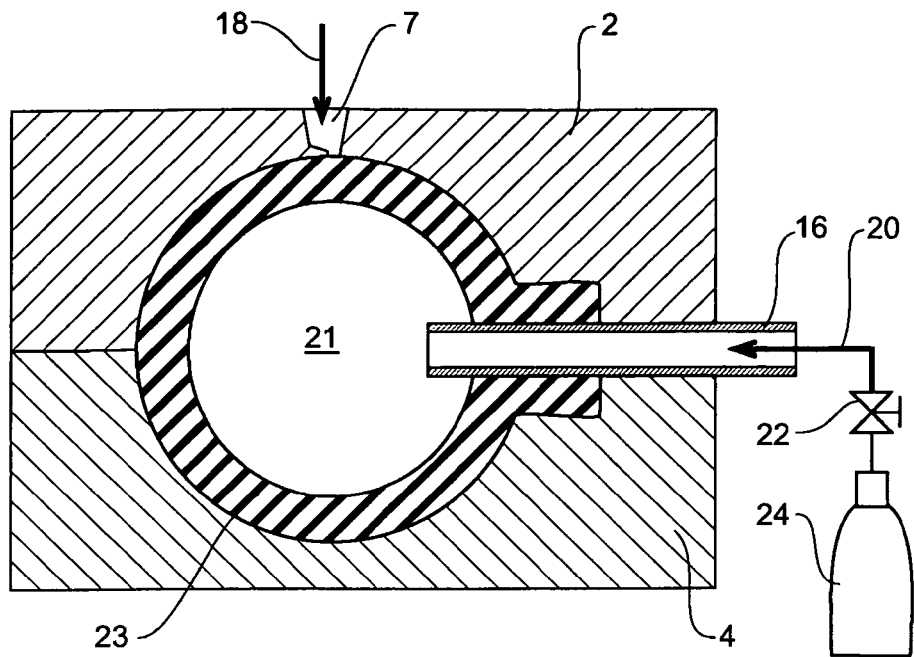
FIG. 3 shows the next stage in the process with mouldable material injected in and gas also injected through the hollow tubular insert.

Now looking more closely at the drawings and in particular the embodiment shown in FIGS. 1 to 5 it will be seen that the mould assembly generally shown as 1 comprises a first mould half 2 and a second mould half 4 which each have a recess which when the two parts of the mould are brought together form a cavity 6 in the mould assembly. An opening 7 provides a sprue and gate 8 for the injection of mouldable material into the cavity 6 and a recess 10 is formed as two semicircular recesses 12 and 14 in the mould halves to receive a hollow tubular part 16 which extends into the cavity 6, when installed, as can be seen in FIG. 2. The arrangement as seen in FIG. 2 is now ready for injection moulding as shown in FIG. 3. Material 23 has been injected as shown by the arrow 18 into the sprue 7 and a short time after the injection of the mouldable material, air has been injected through the hollow tubular insert as shown by arrow 20 from air supply 24 and controlled by valve 22. By this process a hollow 21 is formed in the mouldable material 23. The air pressure is maintained until the mouldable material is hardened.

As an alternative to air, a dry gas such as nitrogen may be injected through the hollow tubular insert.

Figure 4:
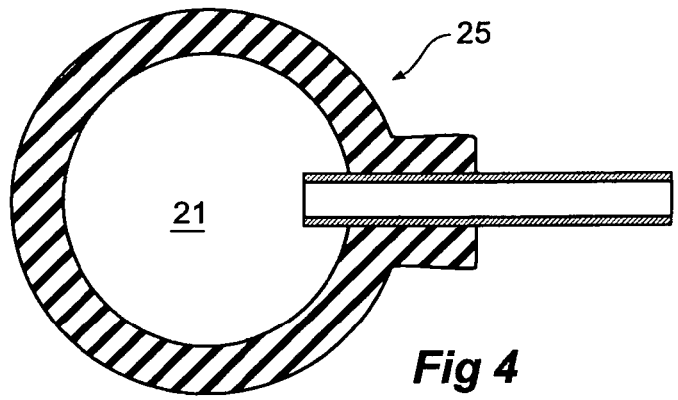
FIG. 4 shows the finished part with a functional cavity formed in it.
Figure 5:
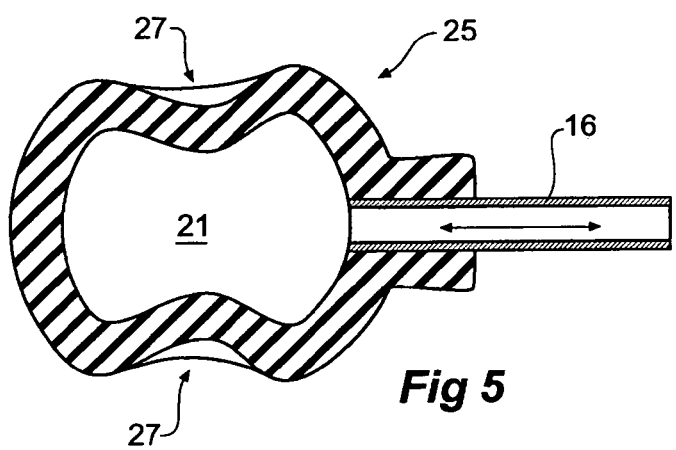
FIG. 5 shows the finished part of FIG. 4 with the sides compressed to act as a pump.

The finished part 25 is then removed from the mould assembly 1 as shown in FIG. 4.

Where the injected material is a resilient material the finished part can be flexed or manipulated to produce a pipette of the like. In FIG. 5 the sides 27 of the moulded part 25 are compressed such as by finger pressure so that fluid within the cavity 21 can travel through the hollow tubular insert 16 which is now moulded into the part so that the part 25 for instance can act as a pipette or some other useful functional device. Hence the cavity is a useful or functional cavity within the part.

It will be realised that if two hollow tubular inserts were used with suitable valve arrangements in them then the part could act, for instance, as a pump, to pump fluid from one insert to another.

Another embodiment of the invention will now be discussed with respect to the moulding of a dual lumen aspiration catheter.

Figure 9:
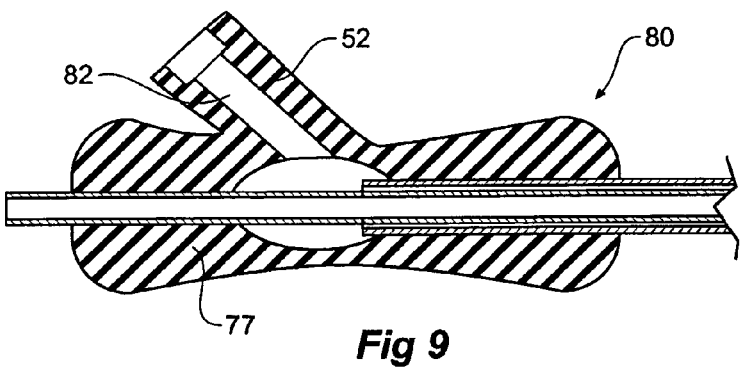
FIG. 9 shows the moulded part after it has been removed from the cavity.
Figure 10:
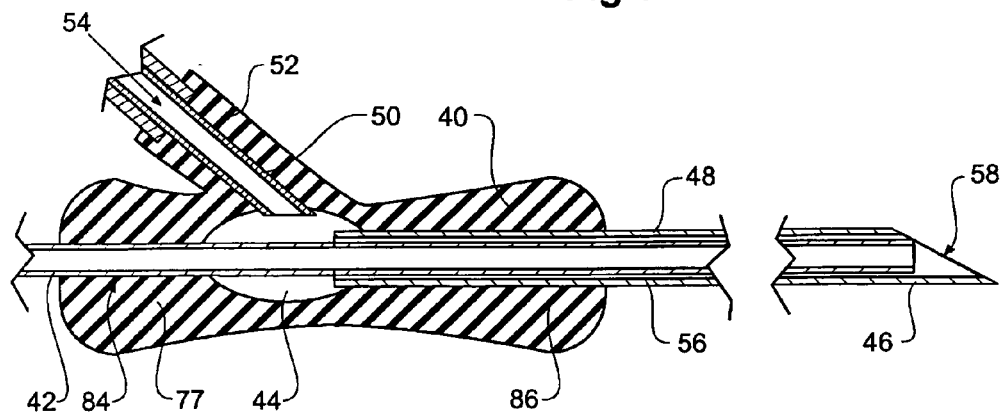
FIG. 10 shows the finished part with a side duct mounted into the finished part.

The aspiration catheter will be initially discussed with respect to FIG. 10 to show the various components and then the moulding of the aspiration catheter can then be discussed with respect to FIGS. 6 to 9.

The aspiration catheter shown in FIG. 10 generally has a handle or body 40 through which passes an aspiration tube 42. The aspiration tube 42 does not open into the cavity 44 within the handle 40 but extends to the tip 58 of a needle cannula 46 which acts as a hollow tubular insert extending into the handle 40 and opening into the cavity 44 within the handle 40. A side tube 50 extends through an arm 52 on the handle 40 and flushing fluid 54 can be supplied through the tube 50 into the cavity 44 and then passed through the annular lumen 56 between the aspiration catheter 42 and the hollow needle 48 so that the flushing fluid can be provided at the needle tip 58 to assist with flushing material into the aspiration catheter 42 to a suitable aspiration system (not shown).

It will be seen that the cavity 44 in this arrangement acts as a functional cavity because it provides a fluid flow junction between the tube 50 in the arm 52 and the needle insert 48 in particular the lumen annular 56 within the needle insert 58 which extends to the needle tip 58.

The moulding of such an assembly is carried out as shown in FIGS. 6 to 9.

Figure 6:
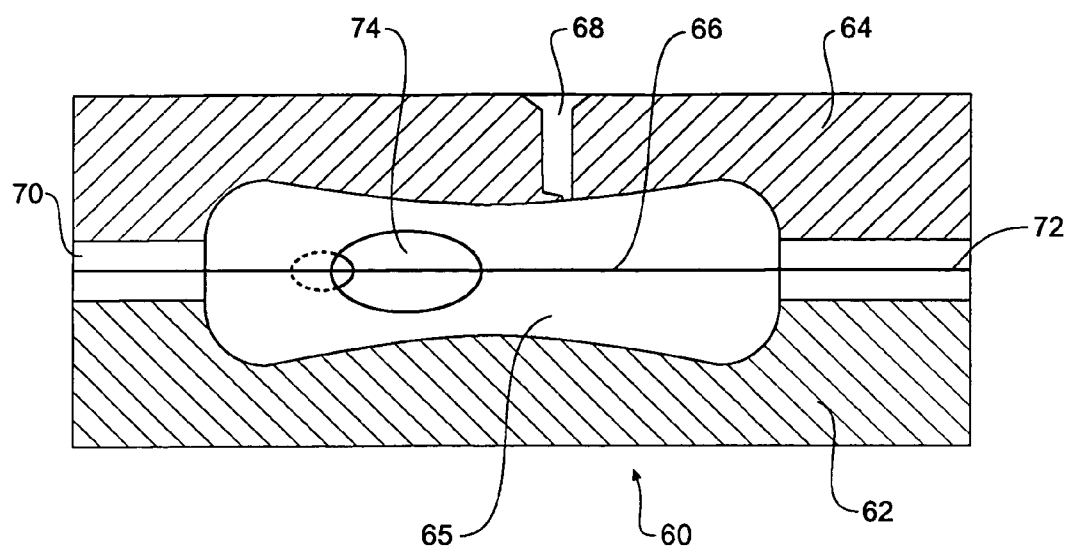
FIG. 6 shows a second embodiment of the invention in the form of a mould assembly in which a handle for an aspiration catheter assembly can be moulded.

FIG. 6 shows a mould assembly 60 comprising a first mould portion 62 and a second mould portion 64. The mould halves join together on a part line 66. Recesses within the mould portions 62 and 64 when they are joined together define the shape of the handle portion of the aspiration catheter. The region 75 defines the main body 40 and the region 74 defines the shape of the arm 52.

Figure 7:
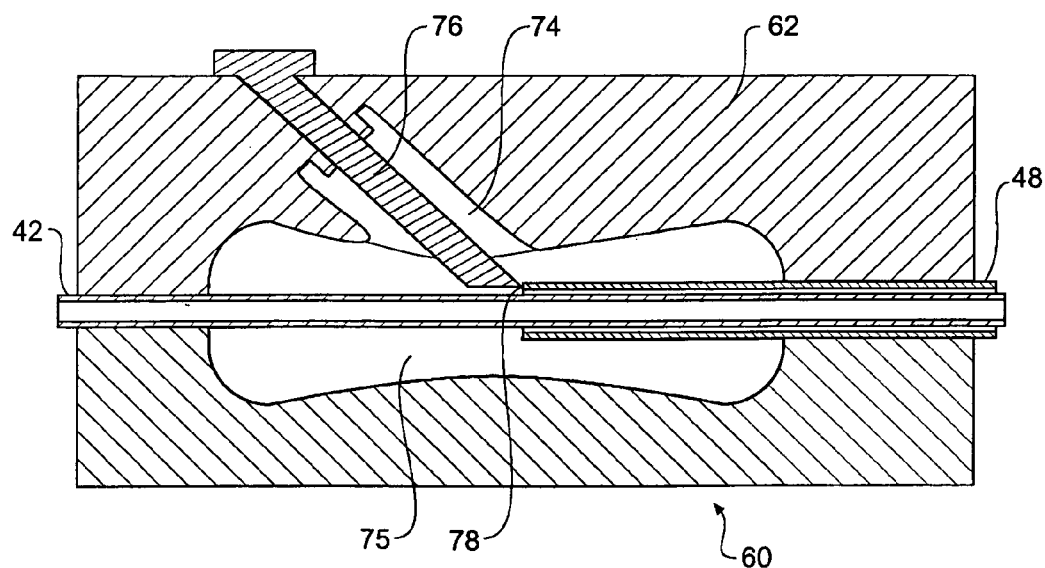
FIG. 7 shows the mould assembly of FIG. 6 with a core and hollow tubular insert arrangement supported in the mould.
Figure 8:
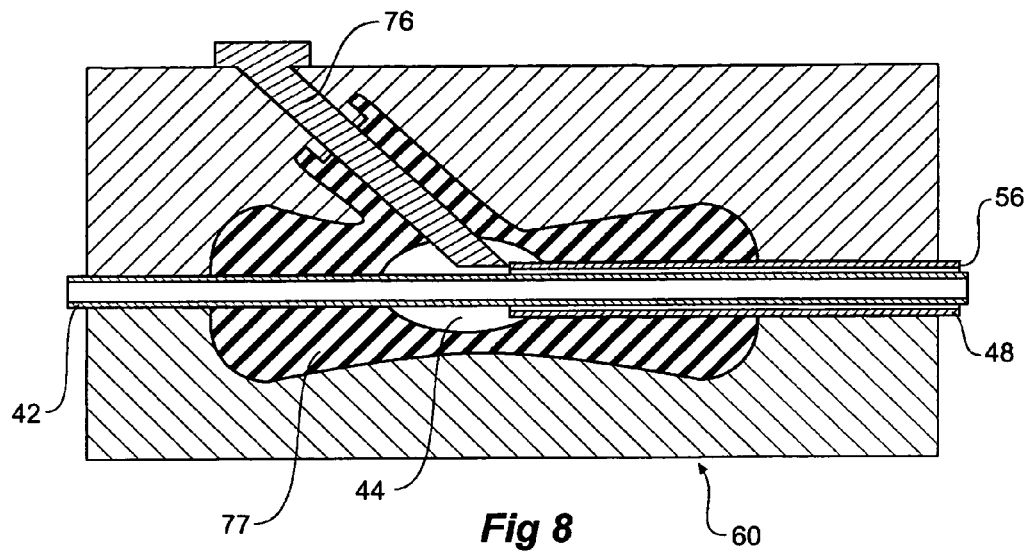
FIG. 8 shows the arrangement of FIG. 7 after injection of mouldable material and gas through the hollow tubular insert.

A sprue arrangement 68 is provided in the mould portion 64. Recesses are provided at 70 and 72 in both mould portions 62 and 64. The recesses 70 when the mould is joined together receive the aspiration cannula 42 and the recess 72 when the mould is joined together receive the hollow tubular needle 48 as can be seen in FIG. 7. The aspiration cannula 42 passes coaxially through the hollow tubular needle 48.

FIG. 7 shows the mould portion 62. To form the hollow duct into which the side tube 50 can be inserted in the arm 52, a void forming core 76 is placed into the region 64 of the mould with the core extending to the inner end 78 of the hollow tube insert 48.

An incomplete shot of plastics material 77 is then provided through the sprue 68 (see FIG. 6) until the mould is partially filled and then air is injected through the annular lumen 56 between the needle 48 and aspiration catheter 42 to form the cavity 44 in the middle of the mouldable material. After cooling, the moulded part, generally shown as 80, is removed from the mould 60 and the core 76 is also removed. This leaves the part as shown in FIG. 9. The tube 50 is then pushed into the hollow aperture 82 left when the core is removed and into the cavity 44 and this enables the fluid connection via the functional cavity 44 between the tube 50 and the lumen 56 as discussed earlier.

If it is desired to make the functional cavity act as a pump then before insertion of the inserts 42 and 48 into the mould, a harder plastic material may be moulded onto the insert 42 in the region 84 and onto the insert 48 in the region 86. The mouldable material from which the handle 40 is made can then be formed from a more elastomeric material, which can give the finished part flexibility sufficient to enable it to be compressed with finger pressure to act as a pump.

It will be realised that other forms of aspiration catheter assemblies can be formed such as single lumen needle systems where a junction is provided in a functional cavity between a flushing fluid entry line 50 and the aspiration cannula 42 and for this purpose the aspiration cannula 42 would have an aperture which when completed would be in the region of the functional cavity 44.

Figure 11A:
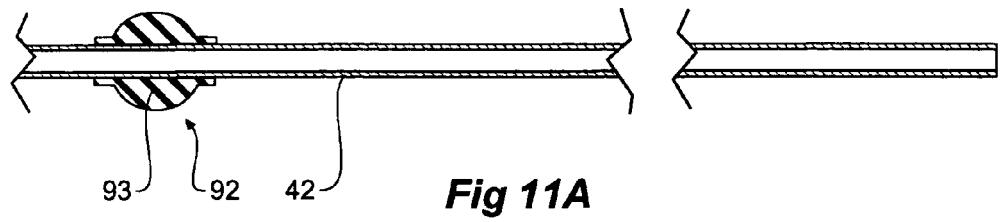
FIGS. 11A and 11B show parts of an aspiration assembly with a hard mouldable material moulded onto the insets of the aspiration catheter as a preliminary step.
Figure 11B:
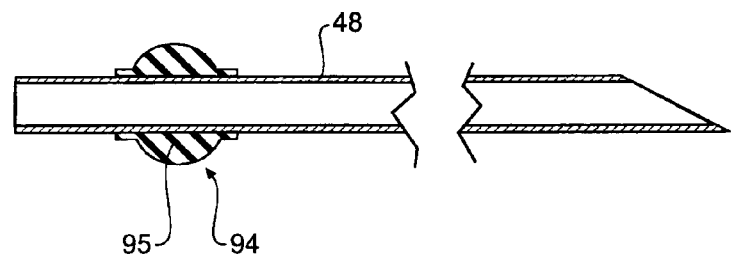

FIGS. 11A and 11B show parts of an aspiration assembly with a hard mouldable material moulded onto the insets of the aspiration catheter as a preliminary step. In FIG. 11A the aspiration cannula 42 has portion of a harder mouldable material 92 such as PVC or styrene moulded onto it in a separate operation. The portion of a harder mouldable material 92 includes wings 93 which provide a greater surface area when the part is moulded into an aspiration assembly. Similarly as shown in FIG. 11B the needle 48 has portion of a harder mouldable material 94 such as PVC or styrene moulded onto it in a separate operation. The portion of a harder mouldable material 94 includes wings 95 which provide a greater surface area when the part is moulded into an aspiration assembly.

Figure 12:
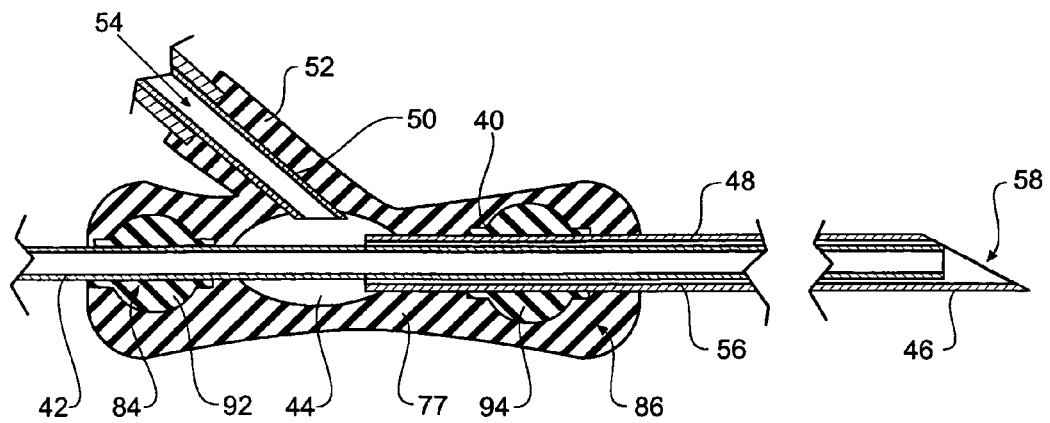
FIG. 12 shows the finished product incorporating the inserts shown in FIGS. 11A and 11B.

FIG. 12 shows the finished product incorporating the inserts shown in FIGS. 11A and 11B. It will be noted that both the added moulded parts 92 and 94 are enveloped with the mouldable material 77. These provide a region of greater surface area and hence adhesion between the mouldable material and the inserts, which will give improved strength.

Figure 13:
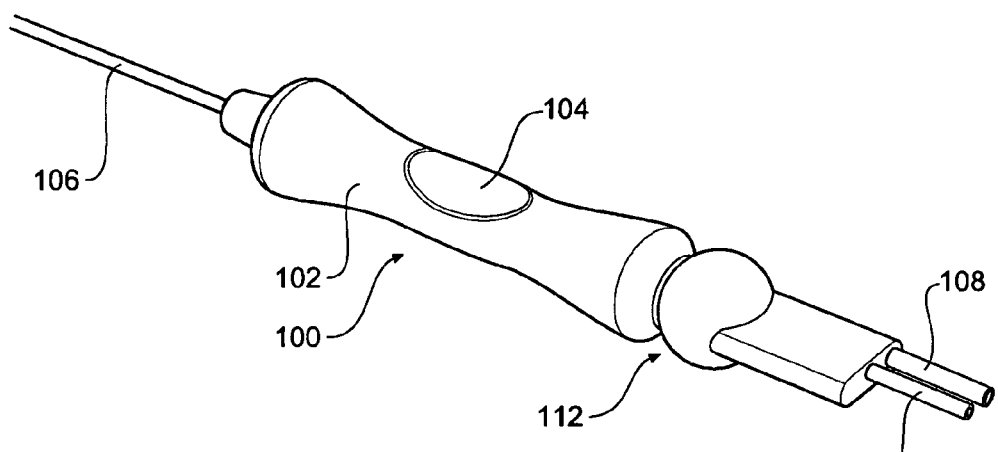
FIG. 13 show an alternative embodiment of aspiration assembly suitable for injection moulding with an functional cavity.
Figure 14:
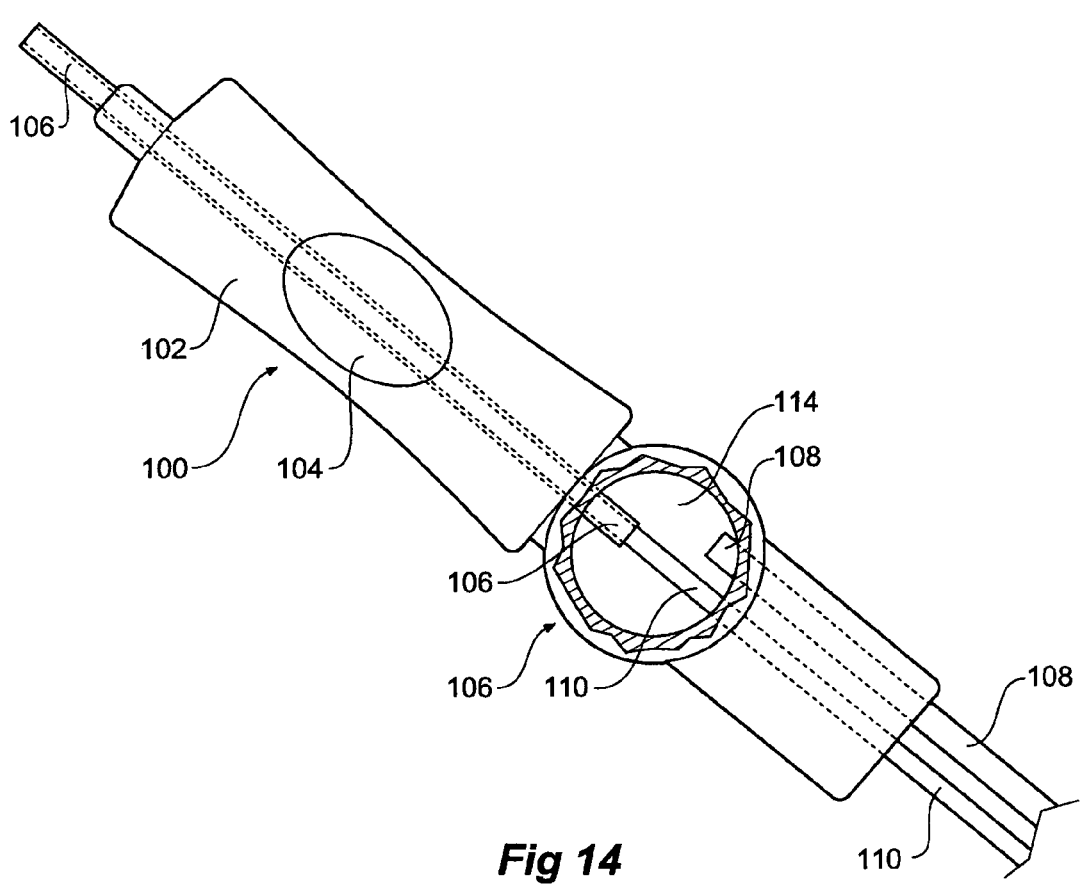
FIG. 14 shows the embodiment of FIG. 13 with part cutaway to show the functional cavity.

FIG. 13 show an alternative embodiment of aspiration assembly suitable for injection moulding with a functional cavity and FIG. 14 shows the embodiment of FIG. 13 with part cutaway to show the functional cavity.

The aspiration assembly 100 has a handle portion 102 with a finger grip 104. A needle cannula 106 extends from one end of the handle 102 and a flushing fluid supply tube 108 and an aspiration cannula 110 extend from the other end of the handle. In the junction portion 112 a functional cavity 114 is formed. The aspiration cannula 110 passes through the functional cavity 114 without opening into it and extends coaxially through the lumen of the needle cannula. Both the flushing fluid supply tube 108 and the annular lumen between the needle cannula 106 and the aspiration cannula 110 open into the functional cavity 114. Gas under pressure can be supplied through each of these to form the functional cavity. In one embodiment, gas is supplied under pressure through each of the entry points to ensure plastics material does not block either entry point.

The size and shape of the functional cavity 110 can be controlled and formed by manipulating the gas pressure from both the flushing fluid supply tube 108 and annular lumen between the needle cannula 106 and the aspiration cannula 110. The timing of the gas flow in and out also prevents the plastic forming a skin over the entry points. In this embodiment nitrogen gas at about 4-bar pressure is used. The bubble size is a balance between gas pressure and shot size.

Throughout this specification, various indications have been given as to the scope of the invention but the invention is not limited to one of these but may reside in two or more of these combined together. The examples are given for illustration only and not for limitation.

What is claimed is:

1. A process of injection moulding a part with a functional cavity including the steps of;

providing a mould assembly comprising at least a first mould portion and a second mould portion which when joined together define a cavity for moulding the part, at least one of the first and second mould portions having an opening therein for allowing injection of a mouldable material into the cavity, a first recess in at least one of the first and second portions, the first recess being to receive a first hollow tubular insert intended to be placed in the mould assembly before the injection of a mouldable material into the cavity and to remain in the part after moulding, a second recess spaced apart from the first recess in at least one of the first and second portions, the second recess being to receive a second hollow tubular insert intended to be placed in the mould assembly before the injection of a mouldable material into the cavity and to remain in the part after moulding and a gas supply arrangement to supply pressurised gas to the first and second hollow tubular inserts during the injection process;

mounting a first hollow tubular insert into the first recess in the mould assembly;

mounting a second hollow tubular insert into the second recess in the mould assembly;

injecting a mouldable material through the opening into the cavity;

injecting a gas under pressure through the first and second hollow tubular inserts into the cavity; and allowing the mouldable material to cool before opening the mould portions to release the moulded part with the first and second hollow tubular inserts retained in the moulded part and opening into the functional cavity;

whereby to allow fluid connection between the first hollow tubular insert and the second hollow tubular insert via the functional cavity.

2. A process as in claim 1 wherein the step of injecting mouldable material into the cavity comprises injection of a less than a complete volume of mouldable material to fill the cavity.

3. A process as in claim 1 wherein the volume of injected material, the time of injection and the pressure of injection and the volume, pressure, temperature and timing of gas injection are selected to give desirable properties and dimensions to the finished product and the functional cavity.

4. A process as in claim 1 wherein the mould assembly further includes a further cavity with a duct extending from the cavity to the further cavity and wherein the step of injecting mouldable material into the cavity comprises injection of a full shot of mouldable material into the mould and then when gas is injected into the mould through the hollow tubular insert, excess mouldable material is passed through the duct from the main cavity Into the further cavity.

5. A process as in claim 1 wherein the step of injecting mouldable material into the cavity includes the step of injecting a full shot of mouldable material and upon injection of the gas, excess mouldable material passing back through the opening back into an injection machine.

6. A process as in claim 1 further including the step of cooling the mould before injection of the gas, so to form a skin on the outer surface of the moulded part.

7. A process as in claim 1 further including a step of moulding a hard mouldable material onto part of the insert to form a coating around the part of the insert before placing the insert into the recess in the mould assembly.

8. A process as in claim 1 wherein the pressurised gas is air or dry nitrogen.

* * * * *